United States Patent
Sumera et al.

(10) Patent No.: US 10,463,590 B1
(45) Date of Patent: Nov. 5, 2019

(54) ANTIPLAQUE AND DENTAL HEALTH ORAL FORMULATION

(71) Applicant: Matthias W Rath, Aptos, CA (US)

(72) Inventors: Waldemar Sumera, Sanjose, CA (US); Matthias W Rath, Aptos, CA (US); Anna Goc, Sanjose, CA (US); Aleksandra Niedzwiecki, Aptos, CA (US)

(73) Assignee: Matthias W. Rath, Aptos, CA (US)

( * ) Notice: Subject to any disclaimer, the term of this patent is extended or adjusted under 35 U.S.C. 154(b) by 0 days.

(21) Appl. No.: 16/226,698

(22) Filed: Dec. 20, 2018

(51) Int. Cl.
| | |
|---|---|
| *A61K 8/49* | (2006.01) |
| *A61K 8/35* | (2006.01) |
| *A61Q 11/00* | (2006.01) |
| *A61K 8/41* | (2006.01) |
| *A61K 8/9789* | (2017.01) |
| *A61K 8/36* | (2006.01) |

(52) U.S. Cl.
CPC ............ *A61K 8/4973* (2013.01); *A61K 8/355* (2013.01); *A61K 8/361* (2013.01); *A61K 8/41* (2013.01); *A61K 8/416* (2013.01); *A61K 8/498* (2013.01); *A61K 8/9789* (2017.08); *A61Q 11/00* (2013.01)

(58) Field of Classification Search
None
See application file for complete search history.

(56) References Cited

U.S. PATENT DOCUMENTS

| | | | | |
|---|---|---|---|---|
| 7,517,541 | B2 * | 4/2009 | Mezine | A61K 8/73 424/401 |
| 2008/0064711 | A1 * | 3/2008 | Friedman | A61K 9/0031 514/277 |
| 2011/0159500 | A1 * | 6/2011 | Khoo | C12Q 1/6883 435/6.12 |

FOREIGN PATENT DOCUMENTS

| | | | | |
|---|---|---|---|---|
| EP | 0256566 A1 * | 2/1988 | | A61K 8/42 |
| WO | WO2000062751 A2 * | 12/2000 | | A61K 7/26 |

OTHER PUBLICATIONS

Gali-Muhtasib et al (Advances in Phytomedicine, vol. 2, 2006, pp. 169-180) (Year: 2006).*

\* cited by examiner

*Primary Examiner* — Celeste A Roney
(74) *Attorney, Agent, or Firm* — Geeta Kadambi; Riddhi IP LLC (57) ABSTRACT

A mixture, comprising at least four different chemical compounds, selected from the group consisting of calcium ascorbate, tocopherol acetate, coenzyme $Q_{10}$, eicosapentaenoic acid, usnic acid, L-carnitine fumarate and norspermidine, is used in dental health compositions. The mixture when used for dental hygiene has bactericidal and bacteriostatic effectiveness against *S. mutans* and *S. sorbinus*.

11 Claims, 12 Drawing Sheets

ANTIPLAQUE AND DENTAL HEALTH ORAL FORMULATION

FIELD OF INVENTION

This invention relates to an oral formulation that prevents dental plaque and improves dental health.

BACKGROUND

The tooth surface is covered with a biofilm—a slime layer consisting of millions of bacterial cells, salivary polymers, and food debris. This biofilm can easily reach a thickness of hundreds of cells on the surfaces of the teeth. The formed biofilm, also called plaque, provides an excellent adhesion site for the colonization and growth of many bacterial species. Bacteria live in these communities to protect themselves from threats like other germs, antibiotics or antimicrobials. The plaque that forms on teeth is a type of dental biofilm, and because it can lead to oral health problems like gum disease or cavities, it needs to be removed promptly. Three effective mechanical methods for biofilm removal are brushing, flossing and furthermore professional cleanings which remove biofilm, plaque and tartar from above and below the gumline with special instruments.

Streptococcus sorbinus is a gram-positive, catalase-negative, non-motile, and anaerobic member of the genus Streptococcus. S. sorbinus in conjunction with the closely related species Streptococcus mutans are pathogenic within humans and enhance the formation of caries within teeth. Biofilm creates a suitable environment for S. sorbinus to grow. S. sorbinus is more closely connected with the prevalence of caries than S. mutans. S. sorbinus is also affiliated with early childhood caries, which is responsible for the majority of dental abscesses and toothaches in children. Children generally acquire S. sorbinus strains from their mother, but the relatively high consumption of sugars by minors facilitates bacterial growth and threatens the onset of early childhood tooth decay. S. sorbinus has also been documented within the teeth of rats.

Streptococcus mutans comprises a group of seven closely related species collectively referred to as the Mutans streptococci. The primary habitats for S. mutans are mouth, pharynx, and intestine. S. mutans and S. sorbinus can adhere to the tooth enamel and to other plaque bacteria and play a central role in the etiology of dental caries. Mutans streptococci are responsible for developing tooth cavities.

Currently, oral biofilm control is primarily accomplished through the use of dentifrice containing compounds such as detergents, abrasives and antimicrobials, which achieve their effects in conjunction with mechanical tooth brushing. If biofilm accumulation and growth can be reduced and its re-aggregation discouraged, this will result in improved gingival health. Conversely, ineffective plaque control is directly implicated in gingival inflammation and eventually in destructive chronic periodontitis. Despite its essential role in the prevention of gingivitis and periodontitis, and often considerable efforts at oral hygiene by patients, effective and stable plaque control remains elusive to many individuals. Accordingly, a multitude of novel anti-plaque formulations are under investigation for their ability to remove oral biofilm and to prevent its re-accumulation.

K. Sahni et al. report in Dentistry (Sunnyvale). 2016 April; 6(4): 371 of an ex vivo study testing the efficacy of the dental debriding formulation HYBENX® Oral Tissue Decontaminant (EPIEN Medical Inc., St. Paul, Minn., USA), for biofilm removal and control. There is a need for enhanced formula for oral hygiene.

SUMMARY

The object underlying the present invention is to provide an anti-plaque composition, which has bactericidal and bacteriostatic effects against S. mutans and S. sorbinus, which prevents the formation of and leads to the removal of dental biofilm and is effective for the prevention and treatment of dental caries.

The object is achieved by a mixture, comprising at least four different chemical compounds, selected from the group consisting of calcium ascorbate, tocopherol acetate, coenzyme $Q_{10}$, eicosapentaenoic acid, usnic acid, L-carnitine fumarate and norspermidine.

The object is furthermore achieved by the use of this mixture as a nutritional supplement composition, in a nutritional supplement composition, in a composition for maintaining dental health, or in anti-plaque, anti-caries or combined anti-plaque/anti-caries dental treatment compositions.

The object is furthermore achieved by a nutritional supplement composition, comprising this mixture. The object is furthermore achieved by a dental health composition or composition for maintaining general dental health, comprising this mixture.

The object is furthermore achieved by an anti-plaque dental composition comprising this mixture in a liquid or paste-like or solid carrier material. The object is furthermore achieved by an anti-caries dental composition comprising this mixture in a liquid or paste-like or solid carrier material.

The object is furthermore achieved by a dental composition with bactericidal and bacteriostatic effectiveness against S. mutans and S. sorbinus, comprising this mixture. The object is furthermore achieved by a composition comprising this mixture for the treatment or prevention of dental caries or dental biofilm.

The object is furthermore achieved by a method for forming a mixture or composition as described above by admixing the ingredients of the mixture or composition.

According to the present invention it has been found that a specific composition of natural compounds has bactericidal and bacteriostatic effects against S. mutans and S. sorbinus, thereby allowing the prevention and treatment of dental caries and dental biofilm.

The specific combination of the ingredients of the composition or mixture leads to a bactericidal and bacteriostatic effect, which is far superior to the effect of each of the ingredients alone.

BRIEF DESCRIPTION OF DRAWINGS

FIG. 7. (A) bacteriostatic effect, FIG. 7(B) bactericidal effect, FIG. 7 (C) preventive effect on biofilm formation, FIG. 7(D) eradicative effect on pre-existing biofilm, FIG. 7(E) biocidal effect on pre-existing biofilm.

DETAILED DESCRIPTION

The mixture according to the present invention comprises at least four different chemical compounds, preferably at least five different chemical compounds, more preferably at least six different chemical compounds, and most preferably all seven of the chemical compounds listed above. In a preferred embodiment, the mixture comprises additionally at least one essential oil as indicated above.

The ingredients per se are known natural compounds. The term "natural compounds" defines compounds that occur in nature or natural products and can be isolated from these natural products. Thus, the term "natural compounds" can be contrasted to "synthetic compounds" which are prepared in a chemical synthesis reaction, whereas the natural compounds are derived from, extracted from or obtained from natural sources. Preferably, the natural compounds discussed below are obtained from natural sources by extraction, distillation, crystallization in a known manner.

The natural compounds employed according to the present invention are:
  calcium ascorbate, also known as vitamin C;
  tocopherol acetate, also known as vitamin E;
  coenzyme $Q_{10}$, also known as ubiquinone, ubidecarenone or coenzyme Q, often abbreviated to $coQ_{10}$;
  eicosapentaenoic acid, often abbreviated as "EPA";
  usnic acid;
  L-carnitine fumarate;
  norspermidine.

The following natural compounds are essential oils which can be obtained, e.g. by extraction, steam distillation or other methods, from the respective plants:
  sage triloba oil also known as sage oil, varieties of which are Dalmatian sage oil, clary sage oil, Spanish sage oil, Greek sage oil, Judaean sage oil;
  Greek sage oil is obtained by steam distillation of *Salvia Triloba* leaves, containing camphor, thujone, and pinene, the dominant component being eucalyptol;
  *Boswellia serrata* oil, derived from *Boswellia serrata*, also known as *Olibanum indicum*;
  clove oil;
  thyme oil;
  cinnamon oil.

Essential oils are concentrated hydrophobic liquids containing volatile aroma compounds from plants. Essential oils are also known as volatile oils, ethereal oils, aetherolea or simply as the oil of the plants from which they were extracted. Some essential oils are known for their medicinal value. For example, thymol is part of a naturally or current type of compounds known as biocides, with strong antimicrobial attributes.

Materials and Methods

Test Compounds.

The following compounds, with the purity between 90%-98% according to the manufacturer, were obtained from Sigma (St. Louis, Mo.): amoxicillin, calcium ascorbate, tocopherol acetate, $CoQ_{10}$, usnic acid, L-carnitine fumarate, norspermidine, clove oil, thyme oil, cinnamon oil, *Boswellia serrata* oil. Eicosapentaenoic acid (EPA) with the purity is between 97% to 99%, according to the manufacturer, was purchased from Cayman Chemical (Ann Arbor, Mich.). Sage triloba oil was from (SunRose Aromatics, Morrill Me.).

Preparation of Test Compounds for Susceptibility Testing.

A stock solution of (10 to 50 mg/ml) of all compounds (depending on solubility of each substance) was prepared by suspending each of the test compounds in DMSO and sterilized by 0.22 μm syringe filtration. All stock solutions were stored in aluminum foil-wrapped tubes at −20° C. Since a high percentage of DMSO could be bactericidal, the amount of DMSO added to the growth medium was kept as low as possible. A preliminary experiment determined that DMSO content should not exceed the maximum percentage of DMSO, established as 0.5% (v/v). In our experiments, the final concentration of DMSO present in the growth medium was kept at or below 0.4% (v/v). The appropriate amount of mixture containing appropriate amount of each stock solution was added to either sterile two-position-cap test tubes containing 1 ml of BHI (Brain Heart Infusion) broth or to 96-well plates containing 200 μl of BHI broth. As a negative control, DMSO at 0.1 to 0.4% (v/v) was applied. As a positive control, amoxicillin at 10 to 500 μg/ml concentration range was used, which is used as a standard antibiotic in treatment of oral infections.

Test Microorganisms.

Two oral *Streptococcus* species, i.e., *Streptococcus mutans* AU159 strain and *Streptococcus sorbinus* SL1 strain, obtained from the American Type Culture Collection (Manassas, Va.), were tested in their two morphological forms: cocci planktonic form and biofilm. The stocks of both species were cultured in commonly used conditions, i.e., BHI broth (Remel, San Diego, Calif.) without antibiotics at 37° C. with 5% $CO_2$, in sterile two-position cap 5 ml polypropylene test tubes.

Evaluation of Bacteriostatic Effect of Test Mix on Oral *Streptococcus* Spp.

Growth inhibition of *Streptococcus mutans* and *Streptococcus sorbinus* was tested using standard macro-dilution method according to guidance of American Society for Microbiology to establish MIC (Minimal Inhibitory Concentration) value. Briefly, sterile 3 ml test two-position capped tubes containing 1 ml BHI broth, supplemented with the test mix was inoculated with $1 \times 10^7$ CFU/ml of the homogenous bacterial suspension. The tubes were then incubated at 37° C. with 5% $CO_2$ and growth inhibition as a decrease in the optical density ($OD_{600}$) was measured after 24 h. The entire experiment was repeated three times for each strain. Control cultures were treated with DMSO (i.e., 0.1-0.4% v/v) alone or amoxicillin (i.e. 10 μg/ml).

Evaluation of Bactericidal Effect of Test Mix on Oral *Streptococcus* Spp.

Killing efficacy against *Streptococcus mutans* and *Streptococcus sorbinus* was determined from macro-broth dilution minimum inhibitory concentration by sub-culturing it to BHI agar plates that do not contain the test mix, which is a standard procedure, performed according to guidance of American Society for Microbiology, to establish MBC (Minimal Bactericidal Concentration) value. Briefly, samples with visible growth inhibition after 24 h incubation with the test mix were plated on sterile BHI agar plates that do not contain the test mix. The plates were then incubated at 37° C. with 5% $CO_2$ and bacterial re-growth was assessed after 24 h. The entire experiment was repeated three times for each strain. Control cultures were treated with DMSO (i.e., 0.1-0.4% v/v) alone or amoxicillin (i.e. 10 µg/ml).

Evaluation of Preventive Effect of Test Mix on Oral *Streptococci* Biofilm Formation.

Preventive effect of the test mix against biofilm of *Streptococcus mutans* and *Streptococcus sorbinus* was evaluated by the commonly used crystal violet (CV) staining method, according to guidance of American Society for Microbiology to establish MBFC (Minimal Biofilm Formation Concentration) value. Briefly, 1×10⁷ CFU/ml from homogeneous bacterial culture in BHI broth containing 1% sucrose, as a standard approach, was inoculated into saliva-coated 96-well plates and supplemented with the test mix. Control wells were treated with DMSO (i.e., 0.1-0.4% v/v) alone or amoxicillin (i.e., 10 µg/ml). All plates were then incubated at 37° C. with 5% $CO_2$ for 24 h. Next, all wells were fixed with 200 µl of cold methanol-formalin (1:1) for 30 min. and stained with 200 µl of crystal violet (0.1%) for 10 min. The biofilms were carefully washed three times with 1×PBS (phosphate-buffered saline), and 200 µl of methanol was added to each well to extract a dye which was measured at 595 nm using a spectrophotometer (Molecular Device, Spectra Max 340). The whole experiment was repeated three times for each strain and each compound/mix.

Evaluation of Eradication Effect of Test Mix on Oral *Streptococci* Pre-Existing Biofilm.

Qualitative and quantitative efficacy of the test mix against biofilm of *Streptococcus mutans* and *Streptococcus sorbinus* was evaluated by the commonly used crystal violet (CV) staining method supported by alamarBlue staining assay (where resazurin, a non-fluorescent indicator dye, is converted to bright red-fluorescent resorufin via the reduction reactions of metabolically active cells and the amount of fluorescence produced is proportional to the number of living cells) for evaluating cellular health, according to guidance of American Society for Microbiology and manufacturer's protocol to establish MBEC (Minimal Biofilm Eradication Concentration) and MBBC (Minimal Biofilm Biocidal Concentration) values. Briefly, 1×10⁷ CFU/ml from homogeneous bacterial culture in BHI broth containing 1% sucrose, as a standard approach, was inoculated into saliva-coated 96-well plates and supplemented with the test mix. Control wells were treated with DMSO (i.e., 0.1-0.4% v/v) alone or amoxicillin (i.e. 500 µg/ml). All plates were then incubated at 37° C. with 5% $CO_2$ up to 24 h. Next, all wells were washed with 1×PBS and supplemented with 10% ready-to-use alamar Blue dye and read with spectrophotometer using 535EX nm/595EM nm filter settings followed by fixation with 200 µl of cold methanol-formalin (1:1) for 30 min. and staining with 200 µl of crystal violet (0.1%) for 10 min. After the biofilms were carefully washed three times with 1×PBS, 200 µl of methanol was added to each well to extract a dye which was measured at 595 nm using a spectrophotometer (Molecular Device, Spectra Max 340). The whole experiment was repeated three times for each strain and each compound/mix.

Evaluation of Pulsing Effect of Test Mix on Oral *Streptococci* Pre-Existing Biofilm.

Pulsing effect of the test mix against mature biofilm of *Streptococcus mutans* and *Streptococcus sorbinus* was evaluated by the commonly used crystal violet (CV) staining method supported by alamarBlue staining assay (where resazurin, a non-fluorescent indicator dye, is converted to bright red-fluorescent resorufin via the reduction reactions of metabolically active cells and the amount of fluorescence produced is proportional to the number of living cells) for evaluating cellular health, according to guidance of American Society for Microbiology and manufacturer's protocol to establish MBEC (Minimal Biofilm Eradication Concentration) and MBBC (Minimal Biofilm Biocidal Concentration) values. Briefly, 1×10⁷ CFU/ml from homogeneous bacterial culture in BHI broth containing 1% sucrose, as a standard approach, was inoculated into saliva-coated 96-well plates and supplemented with the test mix. Control wells were treated with DMSO (i.e., 0.1-0.4% v/v) alone. Treatment was as follow: 10 minutes incubation with the test mix followed by 8 h recovery period in BHI broth supplemented with 1% sucrose. This course was repeated two more times over period of 24 h. All plates were incubated at 37° C. with 5% $CO_2$. Next, all wells were washed and supplemented with 10% ready-to-use alamarBlue dye and read with spectrophotometer using 535EX nm/595EM nm filter settings followed by fixation with 200 µl of cold methanol-formalin (1:1) for 30 min. and staining with 200 µl of crystal violet (0.1%) for 10 min. After the biofilms were carefully washed three times with 1×PBS, 200 µl of methanol was added to each well to extract a dye which was measured at 595 nm using a spectrophotometer (Molecular Device, Spectra Max 340). The whole experiment was repeated three times for each strain and each compound/mix.

Statistical Analysis.

All the data are presented as means±SD (n=3). The Student's two-tailed t test was used to determine statistically significant differences set at 0.05 levels. Statistical analysis was performed using GraphPad software.

In a more preferred embodiment, the mixture comprises sage triloba oil, *Boswellia serrata* oil and at least one additional essential oil, selected from the group consisting of clove oil, thyme oil and cinnamon oil.

The respective chemical compounds and essential oils can be present in the mixture in varying relative amounts. Preferably, the respective chemical compounds and essential oils, if present, are present in the mixture in the following relative amounts: 2 to 50 parts by weight of calcium ascorbate, 6 to 150 parts by weight of tocopherol acetate, 2 to 50 parts by weight of coenzyme $Q_{10}$, 2 to 50 parts by weight of eicosapentaenoic acid, 4 to 100 parts by weight of usnic acid, 4 to 100 parts by of L-carnitine fumarate, 40 to 1000 parts by weight of norspermidine, 40 to 1000 parts by weight of sage triloba oil, 40 to 1000 parts by weight of *Boswellia serrata* oil, 40 to 1000 parts by weight of clove oil, 40 to 1000 parts by weight of thyme oil, 40 to 1000 parts by weight of cinnamon oil.

More preferably, they are present in the following relative amounts: 5 to 20 parts by weight of calcium ascorbate, 15 to 60 parts by weight of tocopherol acetate, 5 to 20 parts by weight of coenzyme $Q_{10}$, 5 to 20 parts by weight of eicosapentaenoic acid, 10 to 40 parts by weight of usnic acid, 10 to 40 parts by weight of L-carnitine fumarate, 100 to 400 parts by weight of norspermidine, 100 to 400 parts by weight of sage triloba oil, 100 to 400 parts by weight of *Boswellia serrata* oil, 100 to 400 parts by weight of clove oil, 100 to 400 parts by weight of thyme oil, 100 to 400 parts by weight of cinnamon oil.

The mixture according to the invention can be used as such or combined with a liquid or paste-like or solid carrier material, which consequently leads to a liquid, paste-like or solid formulation of the mixture. The carrier material allows for a dilution of the mixture and for adjusting the viscosity and rheology of the mixture for a desired way of application.

The mixture can be used as a nutritional supplement composition, in a nutritional supplement composition or in a composition for maintaining dental health. The mixture as such can therefore be the nutritional supplement composition which can supplement other nutritional products since it is composed on natural ingredients. Additional nutritional components like minerals, further vitamins or other acceptable ingredients for nutritional compositions may be present. Thus, the mixture can be used in a nutritional supplement composition of this type.

The mixture can also be used in a composition for maintaining general dental health, i.e. without involving a dedicated pharmaceutical activity. On the other hand, when maintaining general dental health, the mixture or composition according to one embodiment of the invention maintains the general dental health due to possible bactericidal and bacteriostatic effectiveness, or by the prevention of dental biofilm formation. The invention thus also relates to a nutritional supplement composition, comprising the mixture according to the present invention.

Furthermore, the invention relates to a dental health composition, comprising the mixture according to the present invention. One example of a dental health composition is a composition, e.g. a mouth-rinse composition, for the prevention of dental biofilm which can be a non-pharmaceutical application.

As a nutritional supplement composition, nutritional supplement paste, mouth-rinse or mouthwash composition for general dental health, the respective mixture or composition does not classify as a drug or pharmaceutical.

If employed as a mouthwash, the mixture should be in an easily flowing composition, most preferably a liquid composition. For toothpaste, on the other hand, the mixture is preferably present in a paste-like composition. When used as a powder or tablet, the mixture is preferably present in a solid composition.

Pharmaceutically acceptable liquid, paste-like in solid carrier materials or carriers are known in the art. Typically, inert pharmaceutically acceptable carriers are employed.

Further ingredients of the different compositions of the invention can be employed if required: for example additional water-insoluble polishing materials may be employed, specifically in toothpastes or dental polishing compositions. Furthermore, aqueous lower aliphatic alcohols may be employed in the composition. Furthermore, non-ionic surfactants may be employed in the compositions. These additional ingredients re described in more detail in U.S. Pat. No. 4,130,637.

The composition according to the present invention is preferably an oral composition intended for oral application. Thus, the carrier should be an orally acceptable vehicle or base for such composition. The composition can be for example selected from a toothpaste, a gel dentifrice, a tooth powder, a mouth-rinse, a mouthwash, a tooth hardener, an anti-calculus composition, a gum, a lozenge or a format suitable applying the composition to an oral surface, teeth, or gums. Respective compositions and ingredients are disclosed in US 2015/0335557 A1.

Water can be contained in the compositions, for example in an amount in the range of from 20 to 75% by weight.

Thickening agents may be present, for example in an amount of from 2 to 50% by weight. Typical orally acceptable thickening agents comprise polyvinylpyrrolidone (PVP), carboxy polymethylene, polyethylene oxide, polyacrylic acid, copolymers of polyacrylic acid, polyacrylate, polyacrylamide, copolymers of polyacrylic acid and polyacryl amide, PVP-vinyl acetate copolymers, carboxy methyl celluloses, carboxy propyl celluloses, polysaccharide gums, proteins or fumed silica.

Dental compositions can further comprise at least one fluoride salt in an amount as to provide a remineralizing and/or anti-caries effect when the dental treatment composition is used on a daily basis. Preferred is a fluoride salt being included in an amount so as to provide fluoride ions in an amount of from 0.025 to 1.5% by weight.

The compositions can comprise a foaming agent, or they can be free from foaming agents. The compositions can contain abrasives or can be substantially void of abrasives. Additional active adjuvants, which can be used, are for example anti-tartar agents, dental anesthetics, gingival soothing agents, stabilizing agents, remineralizing agents, mouth freshening agents and antioxidants. These additives are for example described in WO 2013/055478 A1.

Preferably, the composition does not contain synthetic pharmaceutical and/or chemical compounds like antibiotics. Preferably, the composition does only contain natural compounds in the above sense. The compositions can contain surfactants and/or emulsifiers, which are preferably natural products, like lecithin.

The composition of the present invention comprises the respective chemical compounds and essential oils, if present, preferably in the following amounts: 2 to 50 μg/ml of calcium ascorbate, 6 to 150 μg/ml of tocopherol acetate, 2 to 50 μg/ml of coenzyme $Q_{10}$, 2 to 50 μg/ml of eicosapentaenoic acid, 4 to 100 μg/ml of usnic acid, 4 to 100 μg/ml of L-carnitine fumarate, 40 to 1000 μg/ml of norspermidine, 40 to 1000 μg/ml of sage triloba oil, 40 to 1000 μg/ml of *Boswellia serrata* oil, 40 to 1000 μg/ml of clove oil, 40 to 1000 μg/ml of thyme oil, 40 to 1000 μg/ml of cinnamon oil. Preferably, the amounts are:
5 to 20 μg/ml of calcium ascorbate, 15 to 60 μg/ml of tocopherol acetate, 5 to 20 μg/ml of coenzyme $Q_{10}$, 5 to 20 μg/ml of eicosapentaenoic acid, 10 to 40 μg/ml of usnic acid, 10 to 40 μg/ml of L-carnitine fumarate, 100 to 400 μg/ml of norspermidine, 100 to 400 μg/ml of sage triloba oil, 100 to 400 μg/ml of *Boswellia serrata* oil, 100 to 400 μg/ml of clove oil, 100 to 400 μg/ml of thyme oil, 100 to 400 μg/ml of cinnamon oil.

The composition according to the present invention can be employed as a pharmaceutical or cosmetical composition. For example, the composition is employed as an anti-plaque dental composition or anti-caries dental composition, or as a dental composition effective as bactericidal and bacteriostatic against *S. mutans* and *S. sorbinus*. Thus, the composition can be a pharmaceutical composition comprising the above mixture and preferably additionally a pharmaceutically acceptable liquid or paste-like or solid carrier. The composition can be for the treatment of dental plaque or caries.

As outlined above, the mixture and composition preferably comprise only natural compounds. The mixture and composition can be formed by admixing the ingredients of the mixture or composition. The invention is further illustrated but not limited by the following examples.

EXAMPLES

The efficacy of individual natural compounds and their combinations was tested on different aspects associated with dental health. The tests were conducted on *S. mutans* and *S. sorbinus*. The direct effects of the test compounds on the bacteria and on biofilm formed by these two bacteria species were evaluated.

Figure 1:
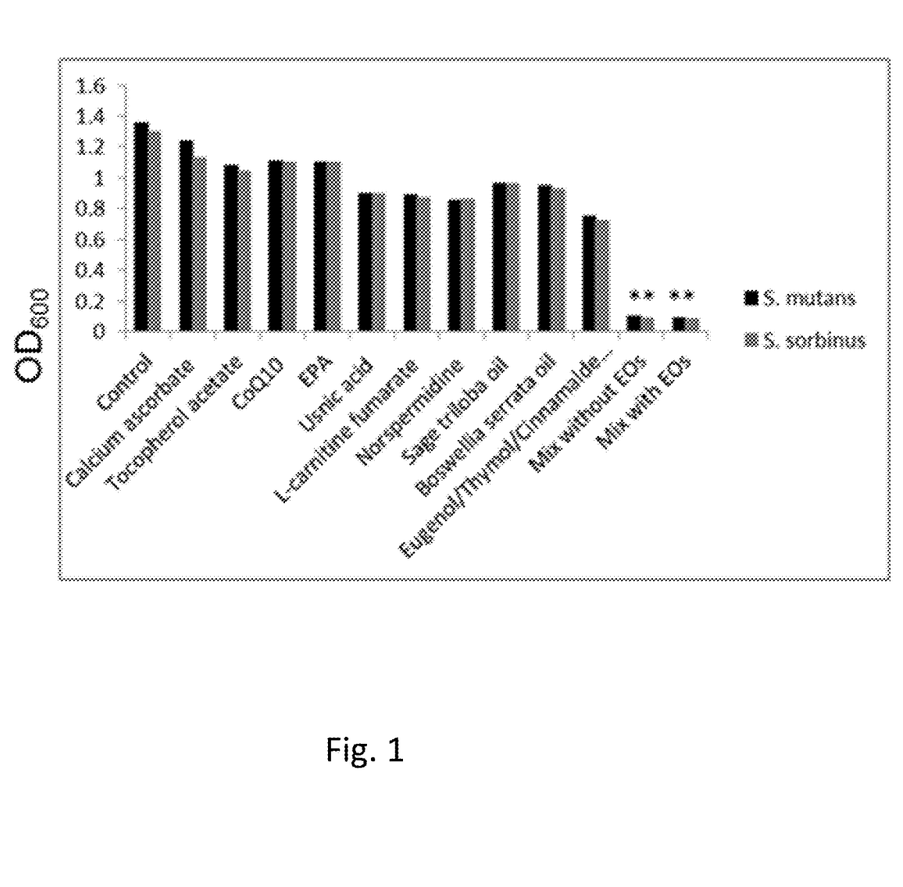
FIG. 1. Shows the bacteriostatic effect of the test mix (including individual compounds present in the test mix) against oral bacterial species, i.e., Streptococcus mutans and Streptococcus sorbinus.

Test compounds included (the concentrations are only valid for FIG. 1 (i.e., bacteriostatic effect)):
calcium ascorbate (vitamin C) 10 μg/ml,
tocopherol acetate (vitamin E) 30 μg/ml,
$CoQ_{10}$ 10 jag/ml,
EPA (eicosapentaenoic acid) 10 jag/ml,
usnic acid 20 jag/ml,
L-carnitine fumarate 20 jag/ml,
norspermidine 200 jag/ml
sage triloba oil 200 jag/ml,
*Boswellia serrata* oil 200 jag/ml,
clove oil 200 jag/ml,
thyme oil 200 μg/ml,
cinnamon oil 200 μg/ml.

These individual compounds and their combinations (with and without essential oils) were tested for bacteriostatic effect (inhibition of bacteria growth) against *S. mutans* and *S. sorbinus* (FIG. 1). The mixture of micronutrients had superior bacteriostatic efficacy compared to individual ingredients (about 80% inhibition of growth).

Figure 2:
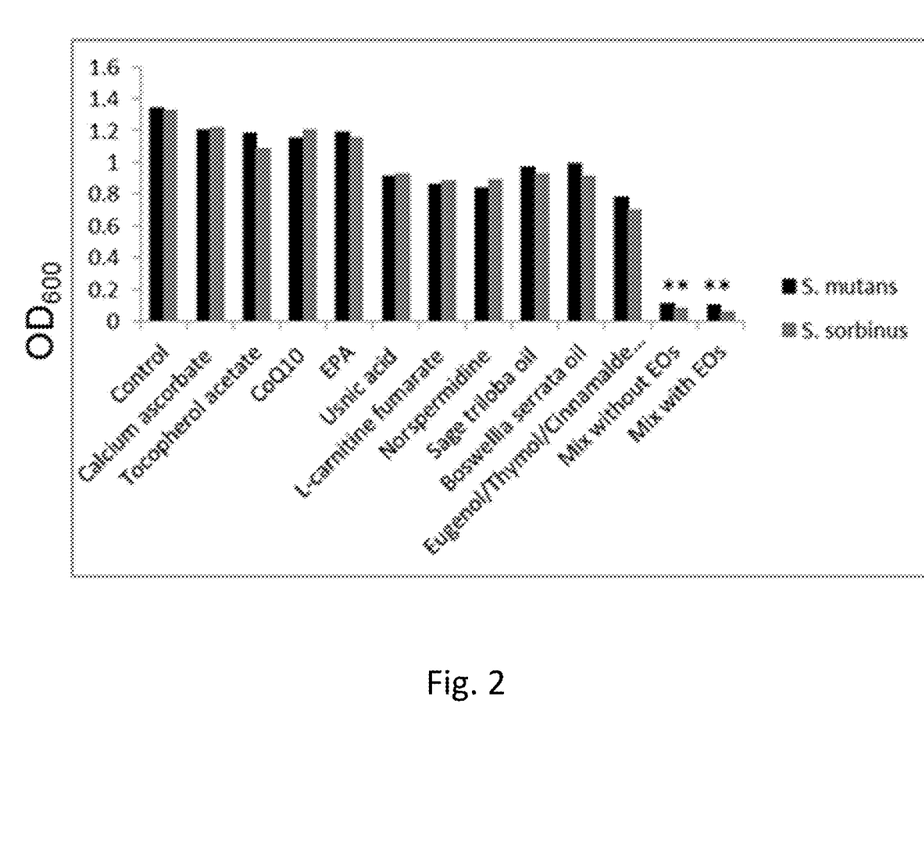
FIG. 2. shows the bactericidal effect of the test mix (including individual compounds present in the test mix) against oral bacterial species, i.e., Streptococcus mutans and Streptococcus sorbinus.

Individual compounds and their combinations (with and without essential oils) were tested for their bactericidal (killing) effect against *S. mutans* and S *sorbinus* (FIG. 2). The mixture demonstrated superior bactericidal efficacy compared to individual components (about 80% bacteria killed).

Figure 3:
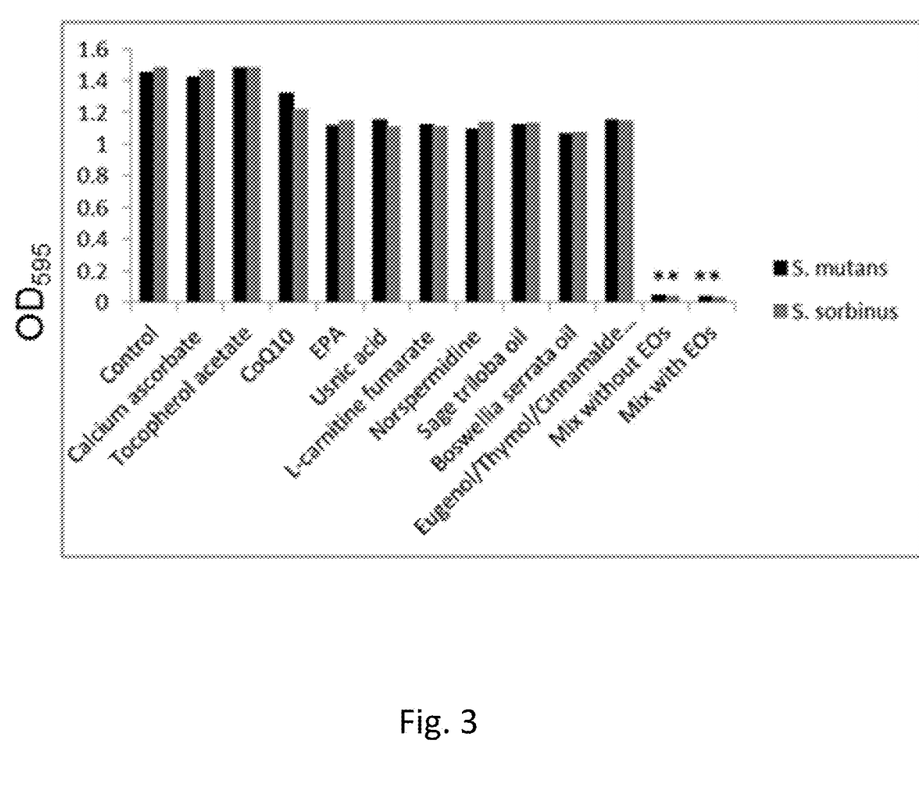
FIG. 3. shows Biofilm growth inhibition (preventive) effect of the test mix (including individual compounds present in the test mix) against oral bacterial species, i.e., Streptococcus mutans and Streptococcus sorbinus.

Individual compounds and their mixture (with and without essential oils) were tested for their ability to prevent the formation of biofilm by these two bacteria species (FIG. 3). The mixture of micronutrients was very effective in almost complete prevention of the biofilm formation compared to individual components. The method we used detects both bacteria and other biofilm components adhering to the test plate.

Figure 4A:
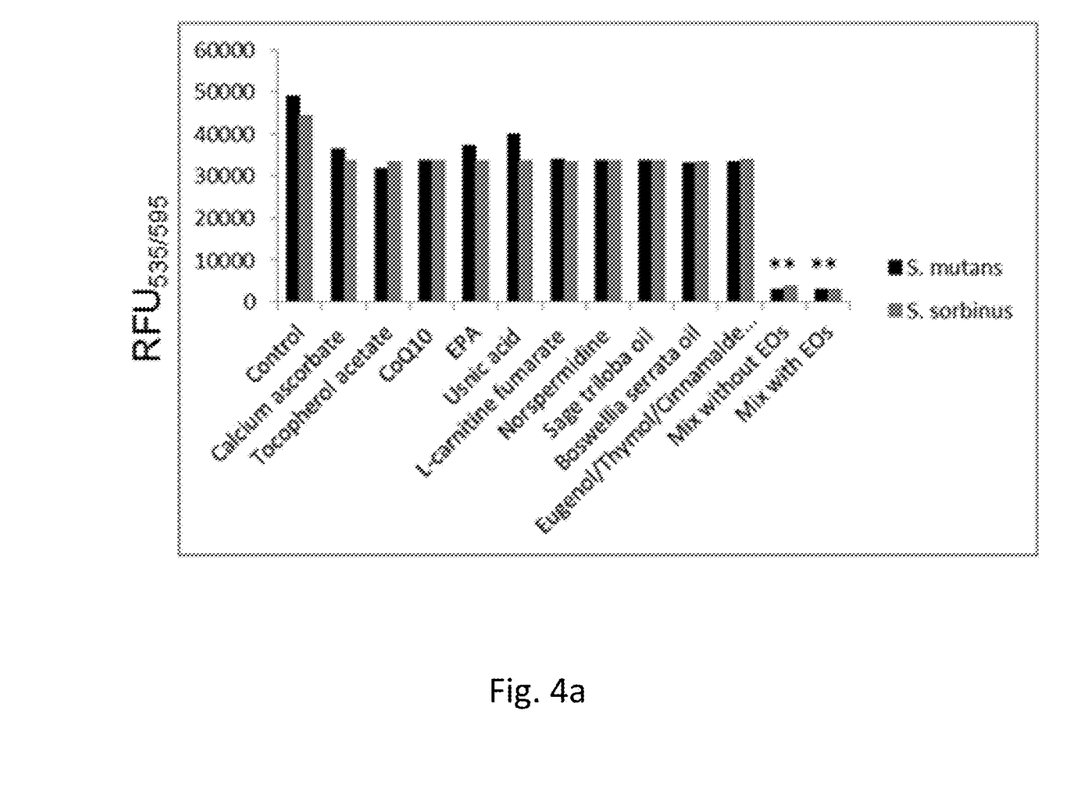
FIG. 4a. shows evaluation of the pre-formed biofilm killing (biocidal) effect of the test mix (including individual compounds present in the test mix) against oral bacterial species, i.e., *Streptococcus mutans* and *Streptococcus sorbinus* determined by alamar Blue assay after 24 h.

Therapeutic effects of individual compounds and their mixture (with and without essential oils) were evaluated on the pre-existing biofilm formed by two bacteria species. The test method allows for detecting the remaining metabolically active and alive bacteria within the biofilm (FIG. 4a). The mixture demonstrated superior efficacy in killing bacteria embedded into previously formed biofilm compared to individual components (around 80-90% bacteria present in biofilm was killed). This implies that an ability of surviving bacteria to re-generate biofilm was significantly reduced.

Figure 4B:
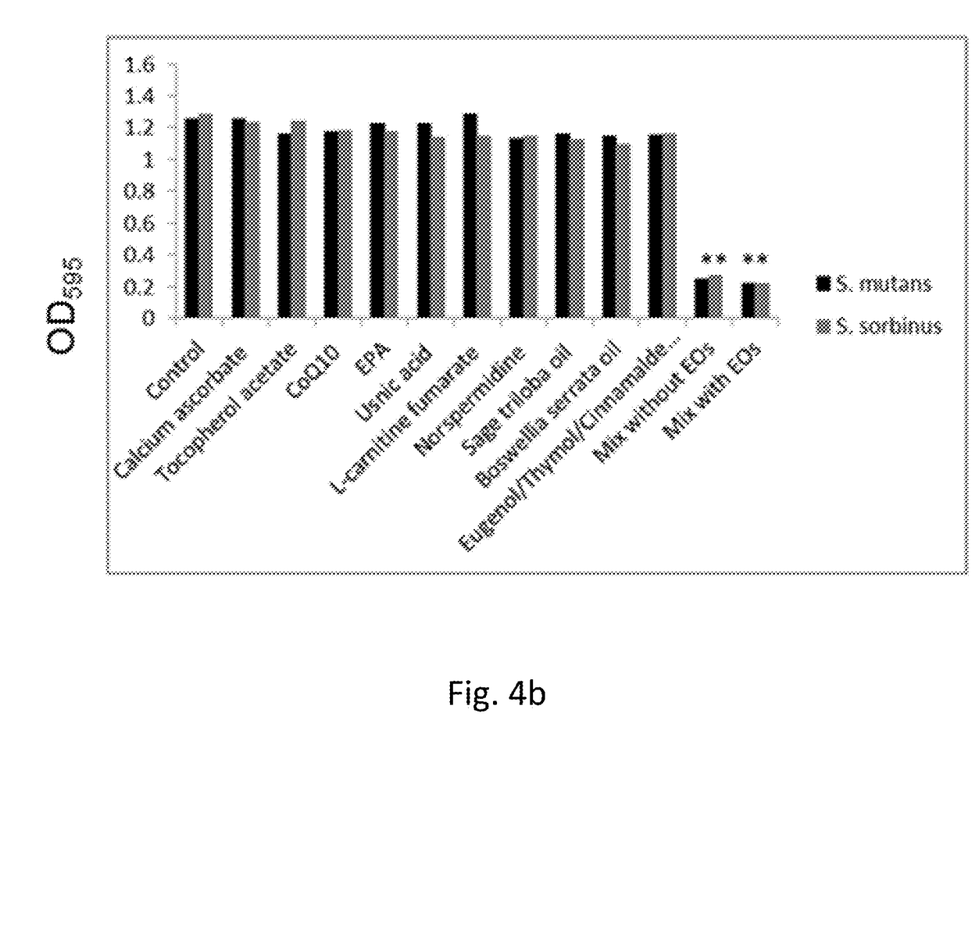
FIG. 4b. Evaluation of the pre-formed biofilm eradicating effect of the test mix.

Therapeutic effects of individual compounds and their mixture (with and without essential oils) on the destruction of existing biofilm. The test compounds and the mixtures were applied continuously for 24 hours on pre-formed biofilm (FIG. 4b). Despite of a low or a lack of efficacy of individual compounds in eradicating pre-existing biofilm, the mixtures was effective in destroying this dental biofilm by about 90%.

Therapeutic effects of interrupted applications of individual compounds and their mixtures (with and without essential oils) on the destruction of biofilm: The treatment (one cycle) involved three courses of 10 minutes each exposure of biofilm to test compounds over 24 hours. This experimental design mimics real life application of the compounds in a form of dental rinse. The evaluation of efficacy was based on testing metabolically active and alive bacteria cells still remaining within a biofilm (FIG. 5), and the extent of biofilm eradication (FIG. 6). Three cycles of exposure of biofilm to test mixtures were very effective in killing bacteria inside the biofilm and it was effective in eradicating in the biofilm in about 75% compared to control. Individual compounds effects varied but showed no more than 50% efficacy.

In addition, the efficacy of an antibiotic (amoxicillin) on two bacteria species and their biofilm was evaluated which confirmed the superior efficacy of the unique natural mixture vs antibiotic treatment (FIG. 7): The results show that while amoxicillin has bacteriostatic and bactericidal effects it is not effective against pre-existing biofilm. The tests and test results are described in the following in more detail.

FIG. 1. Evaluation of the bacteriostatic effect of the test mix (including individual compounds present in the test mix) against oral bacterial species, i.e., *Streptococcus mutans* and *Streptococcus sorbinus* determined by broth macro-dilution assay after 24 h. Tested ingredients: calcium ascorbate 10 μg/ml, tocopherol acetate 30 μg/ml, $CoQ_{10}$ 10 μg/ml, EPA 10 μg/ml, usnic acid 20 μg/ml, L-carnitine fumarate 20 μg/ml, norspermidine 200 μg/ml, sage triloba oil 200 μg/ml, *Boswellia serrata* oil 200 μg/ml, and either clove oil 200 μg/ml or thyme oil 200 μg/ml or cinnamon oil 200 μg/ml; *p≤0.001. 100% bacteriostatic effect was achieved with the test mix at 700 to 900 μg/ml (calcium ascorbate 10 μg/ml, tocopherol acetate 30 μg/ml, $CoQ_{10}$ 10 μg/ml, EPA 10 μg/ml, usnic acid 20 μg/ml, L-carnitine fumarate 20 μg/ml, norspermidine 200 μg/ml, sage triloba oil 200 μg/ml, *Boswellia serrata* oil 200 μg/ml, and either clove oil 200 μg/ml or thyme oil 200 μg/ml or cinnamon oil 200 μg/ml) after 24 h incubation with the test mix against both oral *Streptococcus* spp.

FIG. 2. Evaluation of the bactericidal effect of the test mix (including individual compounds present in the test mix) against oral bacterial species, i.e., *Streptococcus mutans* and *Streptococcus sorbinus* determined by broth macro-dilution combined with plating assay after 24 h. Tested ingredients: calcium ascorbate 10 μg/ml, tocopherol acetate 10 μg/ml, $CoQ_{10}$ 10 μg/ml, EPA 10 μg/ml, usnic acid 50 μg/ml, L-carnitine fumarate 10 μg/ml, norspermidine 250 μg/ml, sage triloba oil 200 μg/ml, *Boswellia serrata* oil 200 μg/ml, and either clove oil 250 μg/ml or thyme oil 250 μg/ml or cinnamon oil 250 μg/ml; *p≤0.001. 100% bactericidal effect was achieved with the test mix at 750 to 1000 μg/ml (calcium ascorbate 10 μg/ml, tocopherol acetate 10 μg/ml, $CoQ_{10}$ 10 μg/ml, EPA 10 μg/ml, usnic acid 50 μg/ml, L-carnitine fumarate 10 μg/ml, norspermidine 250 μg/ml, sage triloba oil 200 μg/ml, *Boswellia serrata* oil 200 μg/ml, and either clove oil 250 μg/ml or thyme oil 250 μg/ml or cinnamon oil 250 μg/ml) after 24 h incubation with the test mix against both oral *Streptococcus* spp.

FIG. 3. Biofilm growth inhibition (preventive) effect of the test mix (including individual compounds present in the test mix) against oral bacterial species, i.e., *Streptococcus mutans* and *Streptococcus sorbinus* determined by crystal violet staining assay after 24 h. Tested ingredients: calcium ascorbate 10 μg/ml, tocopherol acetate 10 μg/ml, $CoQ_{10}$ 10 μg/ml, EPA 10 μg/ml, usnic acid 50 μg/ml, L-carnitine fumarate 10 μg/ml, norspermidine 250 μg/ml, sage triloba oil 200 μg/ml, *Boswellia serrata* oil 200 μg/ml, and either clove oil 250 μg/ml or thyme oil 250 μg/ml or cinnamon oil 250 μg/ml; *p≤0.001. 100% biofilm preventive effect was achieved with the test mix at 750 to 1000 μg/ml (calcium ascorbate 10 μg/ml, tocopherol acetate 10 μg/ml, $CoQ_{10}$ 10 μg/ml, EPA 10 μg/ml, usnic acid 50 μg/ml, L-carnitine fumarate 10 μg/ml, norspermidine 250 μg/ml, sage triloba oil 200 μg/ml, *Boswellia serrata* oil 200 μg/ml, and either clove oil 250 μg/ml or thyme oil 250 μg/ml or cinnamon oil 250 μg/ml) after 24 h incubation with the test mix.

FIG. 4a. Evaluation of the pre-formed biofilm killing (biocidal) effect of the test mix (including individual compounds present in the test mix) against oral bacterial species, i.e., *Streptococcus mutans* and *Streptococcus sorbinus* determined by alamar Blue assay after 24 h. Tested ingredients: calcium ascorbate 10 µg/ml, tocopherol acetate 10 µg/ml, CoQ$_{10}$ 10 µg/ml, EPA 10 µg/ml, usnic acid 50 µg/ml, L-carnitine fumarate 10 µg/ml, norspermidine 250 µg/ml, sage triloba oil 200 µg/ml, *Boswellia serrata* oil 200 µg/ml, and either clove oil 250 µg/ml or thyme oil 250 µg/ml or cinnamon oil 250 µg/ml; *p≤0.001. 100% pre-formed biofilm bactericidal effect was achieved with the test mix at 750 to 1000 µg/ml (calcium ascorbate 10 µg/ml, tocopherol acetate 10 µg/ml, CoQ$_{10}$ 10 µg/ml, EPA 10 µg/ml, usnic acid 50 µg/ml, L-carnitine fumarate 10 µg/ml, norspermidine 250 µg/ml, sage triloba oil 200 µg/ml, *Boswellia serrata* oil 200 µg/ml, and either clove oil 250 µg/ml or thyme oil 250 µg/ml or cinnamon oil 250 µg/ml) after 24 h incubation with the test mix.

FIG. 4b. Evaluation of the pre-formed biofilm eradicating effect of the test mix (including individual compounds present in the test mix) against oral bacterial species, i.e., *Streptococcus mutans* and *Streptococcus sorbinus* determined by crystal violet staining assay after 24 h. Tested ingredients: calcium ascorbate 10 µg/ml, tocopherol acetate 10 µg/ml, CoQ$_{10}$ 5 µg/ml, EPA 10 µg/ml, usnic acid 10 µg/ml, L-carnitine fumarate 5 µg/ml, norspermidine 1000 µg/ml, sage triloba oil 1000 µg/ml, *Boswellia serrata* oil 1000 µg/ml, and either clove oil 500 µg/ml or thyme oil 500 µg/ml or cinnamon oil 500 µg/ml; *p≤0.001. 90% mature biofilm eradication effect was achieved with the test mix at 3050 to 3550 µg/ml (calcium ascorbate 10 µg/ml, tocopherol acetate 10 µg/ml, CoQ$_{10}$ 5 g/ml, EPA 10 µg/ml, usnic acid 10 µg/ml, L-carnitine fumarate 5 µg/ml, norspermidine 1000 µg/ml, sage triloba oil 1000 µg/ml, *Boswellia serrata* oil 1000 µg/ml, and either clove oil 500 µg/ml or thyme oil 500 µg/ml or cinnamon oil 500 µg/ml) after 24 h incubation with the test mix.

Figure 5:
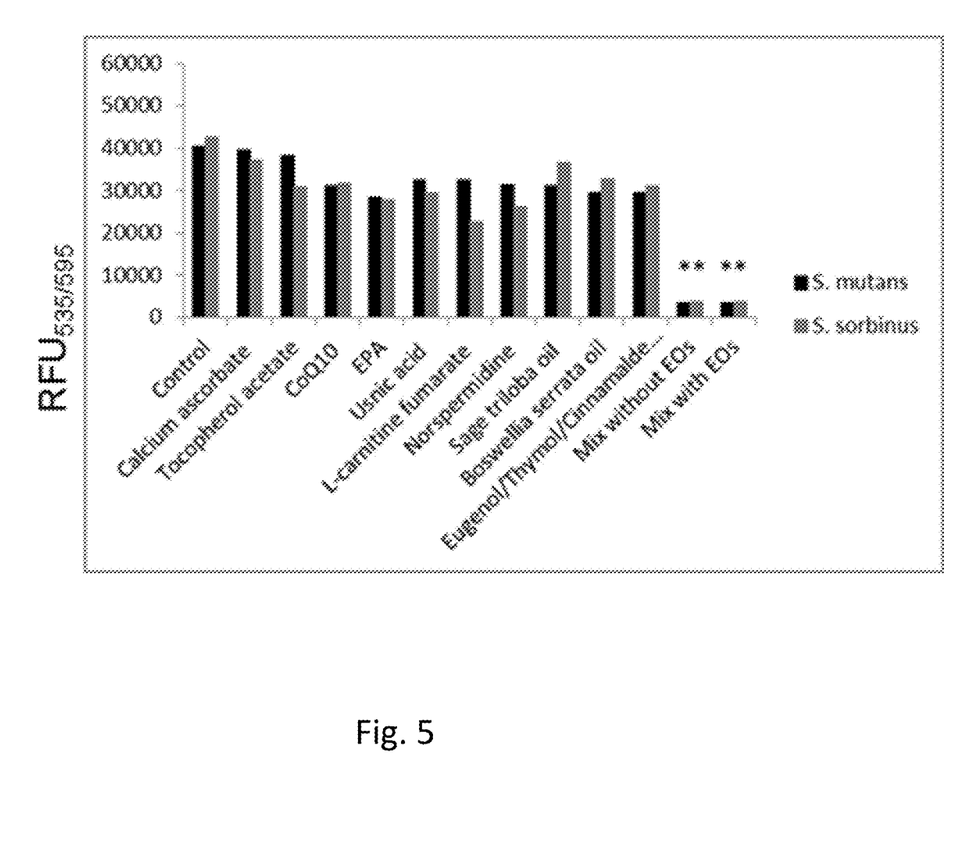
FIG. 5. Pulsing effect of the test mix (including individual compounds present in the test mix) on the killing pre-existing biofilm of oral bacterial species.
Figure 6:
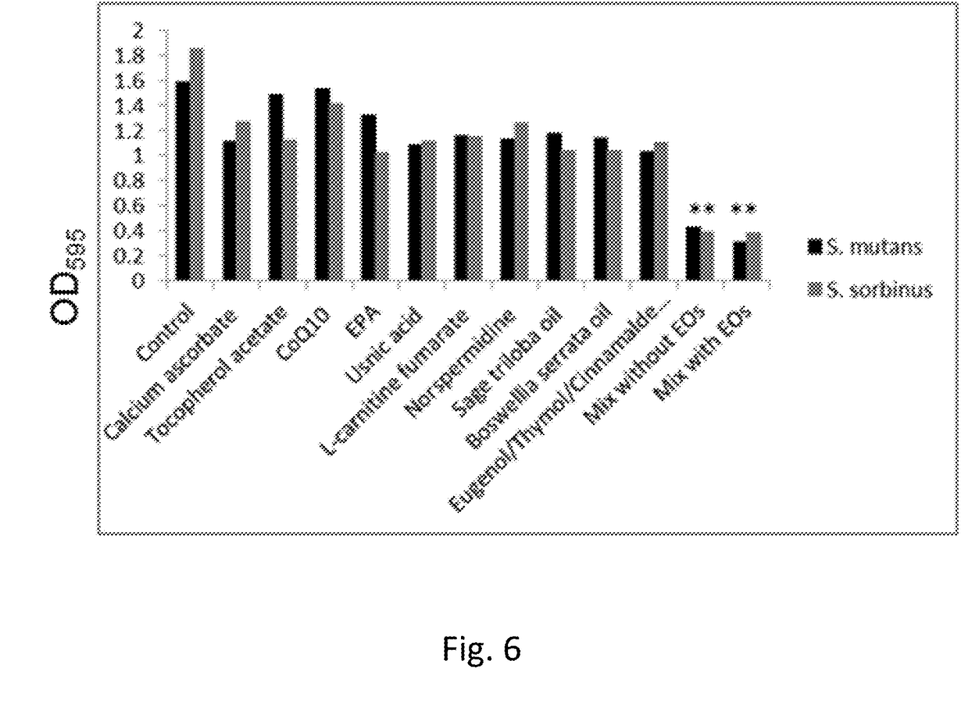
FIG. 6. Shows pulsing effect of the test mix (including individual compounds present in the test mix) on the eradicating pre-existing biofilm of oral bacterial species.
Figure 7A:
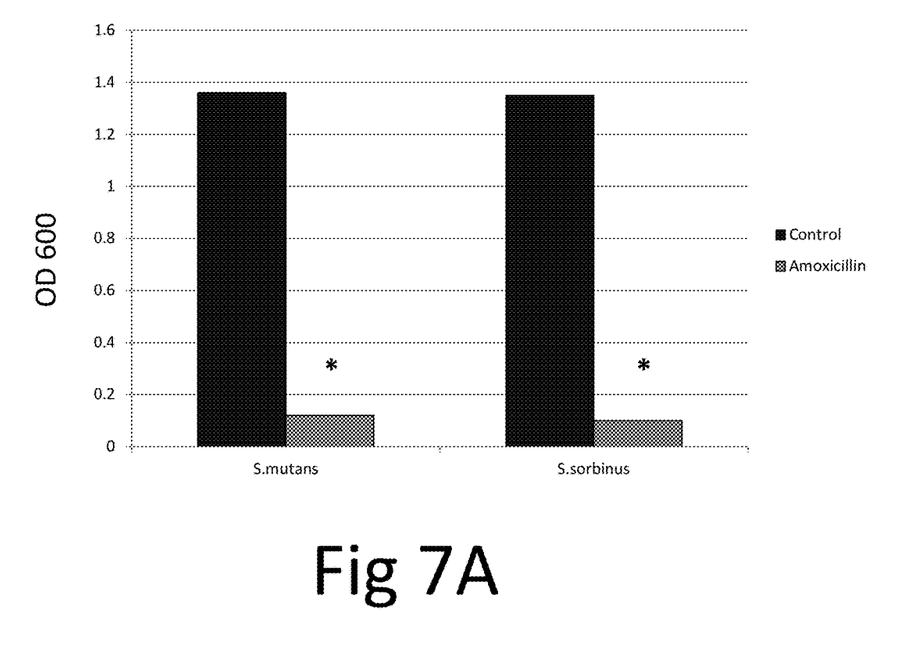
Figure 7B:
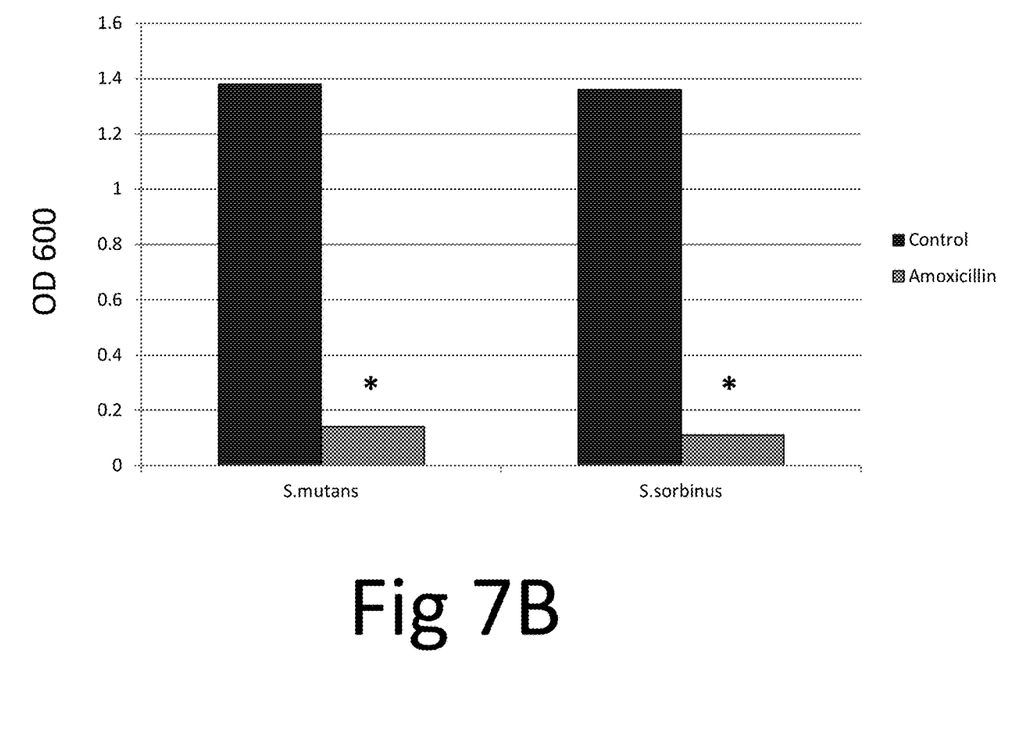
Figure 7C:
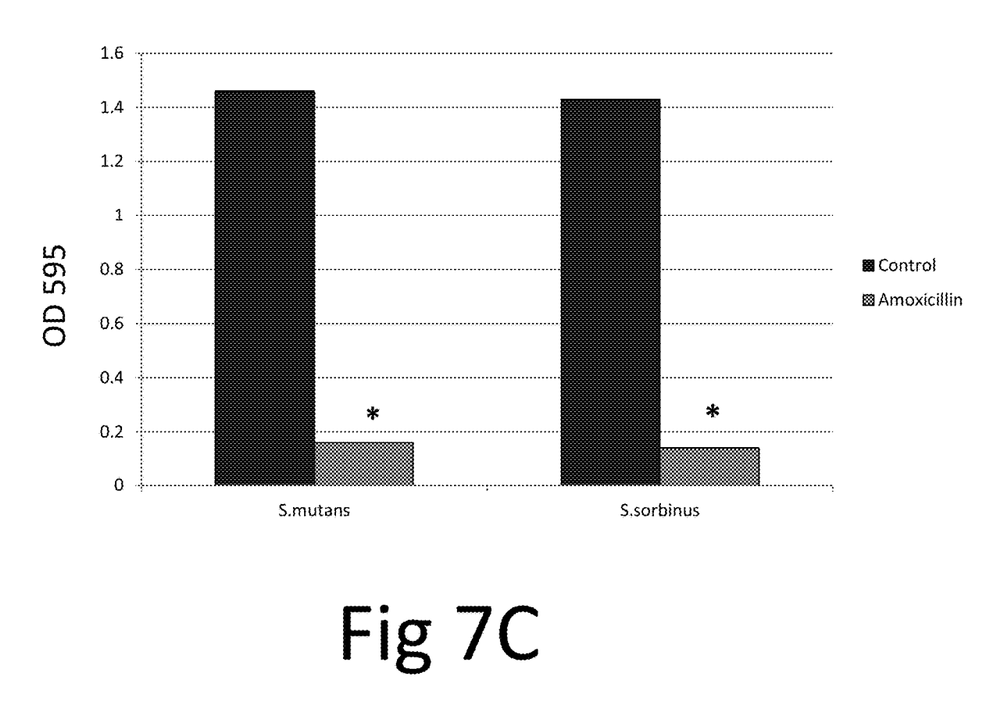
Figure 7D:
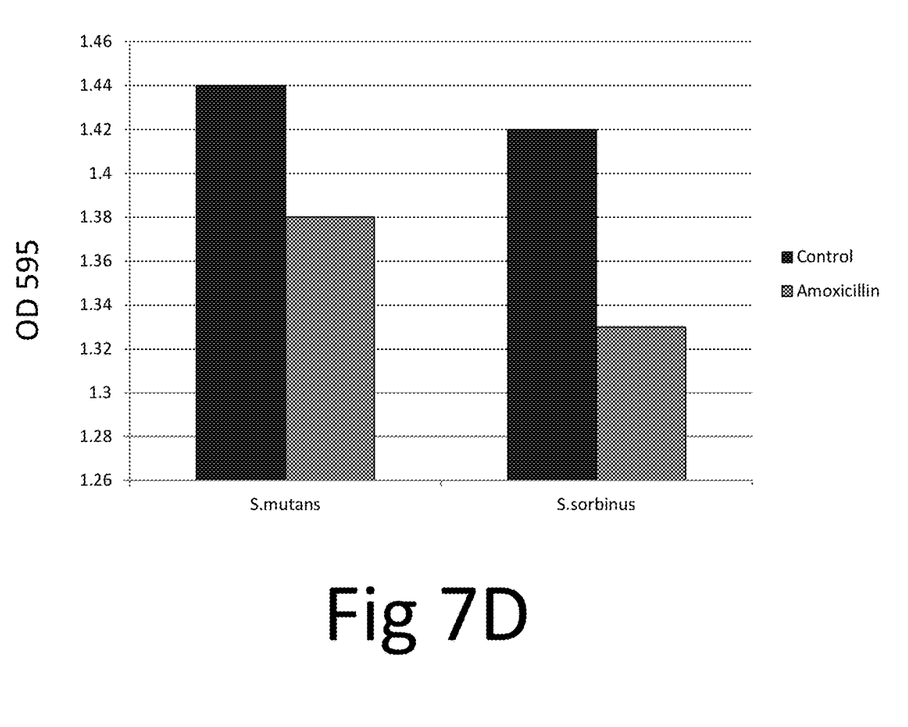
Figure 7E:
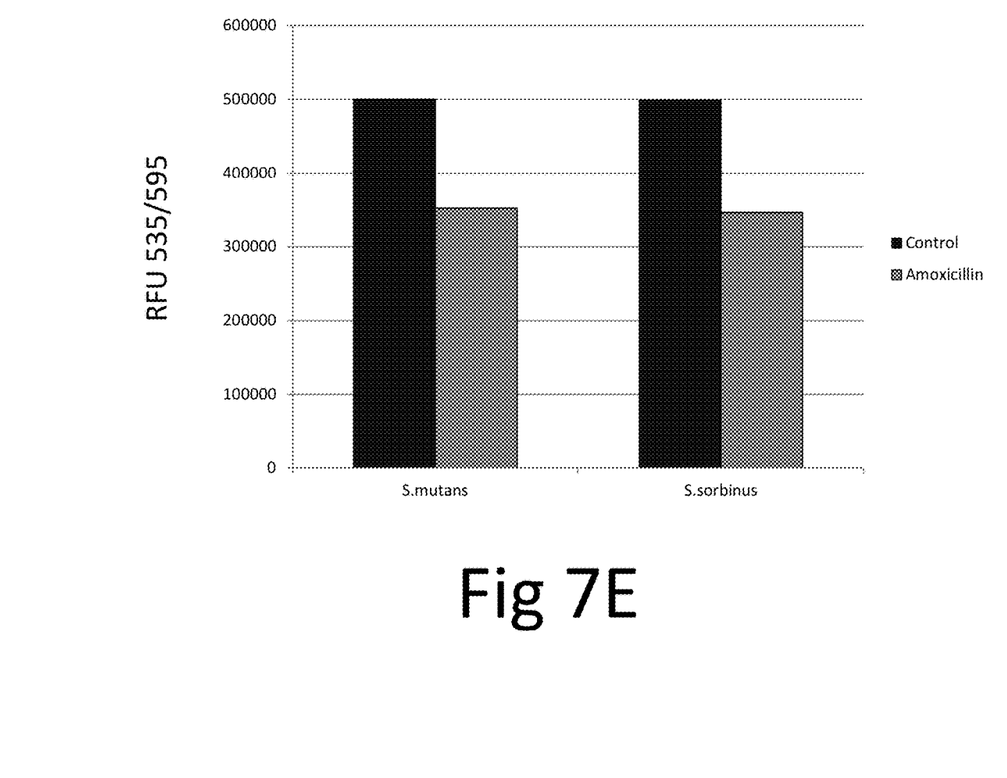

FIG. 5. Pulsing effect of the test mix (including individual compounds present in the test mix) on the killing pre-existing biofilm of oral bacterial species, i.e., *Streptococcus mutans* and *Streptococcus sorbinus* determined by alamar Blue assay after 72 h. Tested ingredients: calcium ascorbate 10 µg/ml, tocopherol acetate 50 µg/ml, CoQ$_{10}$ 10 µg/ml, EPA 10 µg/ml, usnic acid 10 µg/ml, L-carnitine fumarate 20 µg/ml, norspermidine 200 µg/ml, sage triloba oil 200 µg/ml, *Boswellia serrata* oil 200 µg/ml, and either clove oil 250 µg/ml or thyme oil 250 µg/ml or cinnamon oil 250 µg/ml; *p≤0.001. 100% biofilm biocidal efficacy was achieved after the three courses of 10 minutes incubation period with the test mix at 3050 to 3550 µg/ml (calcium ascorbate 10 µg/ml, tocopherol acetate 10 µg/ml, CoQ$_{10}$ 5 µg/ml, EPA 10 µg/ml, usnic acid 10 µg/ml, L-carnitine fumarate 5 µg/ml, norspermidine 1000 µg/ml, sage triloba oil 1000 µg/ml, *Boswellia serrata* oil 1000 µg/ml, and either clove oil 500 µg/ml or thyme oil 500 µg/ml or cinnamon oil 500 µg/ml) over period of 24 h that was repeated for the next 48 h.

FIG. 6. Pulsing effect of the test mix (including individual compounds present in the test mix) on the eradicating pre-existing biofilm of oral bacterial species, i.e., *Streptococcus mutans* and *Streptococcus sorbinus* determined by crystal violet staining assay after 72 h. Tested ingredients: calcium ascorbate 10 µg/ml, tocopherol acetate 10 µg/ml, CoQ$_{10}$ 5 µg/ml, EPA 10 µg/ml, usnic acid 10 µg/ml, L-carnitine fumarate 5 µg/ml, norspermidine 1000 µg/ml, sage triloba oil 1000 µg/ml, *Boswellia serrata* oil 1000 µg/ml, and either clove oil 500 µg/ml or thyme oil 500 µg/ml or cinnamon oil 500 µg/ml; *p≤0.001. Approximately 75% pre-existing biofilm eradication efficacy was achieved after three courses of 10 minutes pulsing with the test mix at 3050 to 3550 µg/ml (calcium ascorbate 10 µg/ml, tocopherol acetate 10 µg/ml, CoQ$_{10}$ 5 µg/ml, EPA 10 µg/ml, usnic acid 10 µg/ml, L-carnitine fumarate 5 µg/ml, norspermidine 1000 µg/ml, sage triloba oil 1000 µg/ml, *Boswellia serrata* oil 1000 µg/ml, and either clove oil 500 µg/ml or thyme oil 500 µg/ml or cinnamon oil 500 µg/ml) over period of 24 h that was repeated for the next 48 h.

FIG. 7. (A) bacteriostatic effect, FIG. 7(B) bactericidal effect, FIG. 7 (C) preventive effect on biofilm formation, FIG. 7(D) eradicative effect on pre-existing biofilm, FIG. 7(E) biocidal effect on pre-existing biofilm; *p≤0.001. Antibacterial effect of amoxicillin on oral bacterial species, i.e., *Streptococcus mutans* and *Streptococcus sorbinus*: 100% bacteriostatic effect of 10 µg/ml amoxicillin 7(A), 100% bactericidal effect of 10 µg/ml amoxicillin 7(B), approximately 99% preventive effect of 10 µg/ml amoxicillin on biofilm formation 7 (C), approximately 5% eradicative effect of 500 µg/ml amoxicillin on pre-existing biofilm 7 (D), approximately 20% biocidal effect of 500 µg/ml amoxicillin on pre-existing biofilm.

What is claimed is:

1. A mixture, consisting of a calcium ascorbate, tocopherol acetate, coenzyme Q$_{10}$, eicosapentaenoic acid, usnic acid, L-carnitine fumarate norspermidine, an essential oil and an additional essential oil.

2. The mixture of claim 1, wherein at least a four different compounds are chosen from the calcium ascorbate, tocopherol acetate, coenzyme Q$_{10}$, eicosapentaenoic acid, usnic acid, L-carnitine fumarate and norspermidine.

3. The mixture of claim 1, wherein the essential oil is selected from the group consisting of a sage triloba oil, *Boswellia serrata* oil, clove oil, thyme oil and cinnamon oil.

4. The mixture of claim 3, wherein the additional essential oil is selected from the group consisting of a clove oil, thyme oil and cinnamon oil.

5. The mixture of claim 4, wherein the mixture is at least in a liquid or paste-like or solid carrier material.

6. The mixture of claim 4, wherein the respective chemical compounds and essential oils, if present, are present in the following relative amounts:
   2 to 50 parts by weight of calcium ascorbate, 6 to 150 parts by weight of tocopherol acetate,
   2 to 50 parts by weight of coenzyme Q$_{10}$, 2 to 50 parts by weight of eicosapentaenoic acid,
   4 to 100 parts by weight of usnic acid, 4 to 100 parts by of L-carnitine fumarate, 40 to 1000 parts by weight of norspermidine, 40 to 1000 parts by weight of sage triloba oil, 40 to 1000 parts by weight of *Boswellia serrata* oil, 40 to 1000 parts by weight of clove oil, 40 to 1000 parts by weight of thyme oil, 40 to 1000 parts by weight of cinnamon oil.

7. The mixture of claim 6, wherein the respective chemical compounds and essential oils, are present in the following relative amounts:
   5 to 20 parts by weight of calcium ascorbate, 15 to 60 parts by weight of tocopherol acetate,
   5 to 20 parts by weight of coenzyme Q$_{10}$, 5 to 20 parts by weight of eicosapentaenoic acid,
   10 to 40 parts by weight of usnic acid, 10 to 40 parts by weight of L-carnitine fumarate, 100 to 400 parts by weight of norspermidine, 100 to 400 parts by weight of sage triloba oil, 100 to 400 parts by weight of *Boswellia serrata* oil, 100 to 400 parts by weight of clove oil, 100 to 400 parts by weight of thyme oil, 100 to 400 parts by weight of cinnamon oil.

8. The mixture of claim 7 is used as a nutritional supplement composition, in a composition for maintaining dental health, or in anti-plaque, anti-caries or combined anti-plaque/anti-caries dental treatment compositions or dental biofilm.

9. The mixture of claim 7, having bactericidal and bacteriostatic effectiveness against *S. mutans* and *S. sorbinus*.

10. The mixture of claim 7, consisting of the respective chemical compounds and essential oils in the following amounts:

2 to 50 µg/ml of calcium ascorbate, 6 to 150 µg/ml of tocopherol acetate, 2 to 50 µg/ml of coenzyme $Q_{10}$, 2 to 50 µg/ml of eicosapentaenoic acid, 4 to 100 µg/ml of usnic acid, 4 to 100 µg/ml of L-carnitine fumarate, 40 to 1000 µg/ml of norspermidine, 40 to 1000 µg/ml of sage triloba oil, 40 to 1000 µg/ml of *Boswellia serrata* oil, 40 to 1000 µg/ml of clove oil, 40 to 1000 µg/ml of thyme oil, 40 to 1000 µg/ml of cinnamon oil.

11. The mixture of claim 10, consisting of the respective chemical compounds and essential oils in the following amounts:

5 to 20 µg/ml of calcium ascorbate, 15 to 60 µg/ml of tocopherol acetate, 5 to 20 µg/ml of coenzyme $Q_{10}$, 5 to 20 µg/ml of eicosapentaenoic acid, 10 to 40 µg/ml of usnic acid, 10 to 40 µg/ml of L-carnitine fumarate, 100 to 400 µg/ml of norspermidine, 100 to 400 µg/ml of sage triloba oil, 100 to 400 µg/ml of *Boswellia serrata* oil, 100 to 400 µg/ml of clove oil, 100 to 400 µg/ml of thyme oil, 100 to 400 µg/ml of cinnamon oil.

* * * * *